US007973085B2

(12) United States Patent
Ishikubo et al.

(10) Patent No.: US 7,973,085 B2
(45) Date of Patent: Jul. 5, 2011

(54) GEL COMPOSITION

(75) Inventors: Akira Ishikubo, Yokohama (JP); Takashi Ohmori, Yokohama (JP); Yuki Suzuki, Yokohama (JP)

(73) Assignee: Shiseido Company Ltd., Chuo-ku, Tokyo (JP)

( * ) Notice: Subject to any disclaimer, the term of this patent is extended or adjusted under 35 U.S.C. 154(b) by 189 days.

(21) Appl. No.: 12/304,173

(22) PCT Filed: Jun. 6, 2007

(86) PCT No.: PCT/JP2007/061420
§ 371 (c)(1),
(2), (4) Date: Dec. 10, 2008

(87) PCT Pub. No.: WO2007/145105
PCT Pub. Date: Dec. 21, 2007

(65) Prior Publication Data
US 2009/0163616 A1    Jun. 25, 2009

(30) Foreign Application Priority Data

Jun. 12, 2006 (JP) ................. 2006-162028
Jan. 22, 2007 (JP) ................. 2007-011982

(51) Int. Cl.
*A01N 25/00* (2006.01)
*A61K 47/00* (2006.01)
(52) U.S. Cl. ........................... 514/772; 514/769
(58) Field of Classification Search .................. 560/198; 568/624; 424/57, 59; 510/112, 132; 514/311, 514/772, 769; 106/243; 507/242
See application file for complete search history.

(56) References Cited

U.S. PATENT DOCUMENTS

| 2,674,619 A | * | 4/1954 | Lundsted | 560/198 |
| 2,828,345 A | * | 3/1958 | Spriggs | 568/624 |
| 3,507,923 A | * | 4/1970 | Bailey et al. | 568/616 |
| 3,579,465 A | * | 5/1971 | Schmolka | 516/102 |

(Continued)

FOREIGN PATENT DOCUMENTS

JP    53-27776    8/1978

(Continued)

OTHER PUBLICATIONS

Japanese Patent Abstract for Publication No. 01-163111 published Jun. 27, 1989, one page, Abstract only.

(Continued)

*Primary Examiner* — James Seidleck
*Assistant Examiner* — Peter A Salamon
(74) *Attorney, Agent, or Firm* — Rankin, Hill & Clark LLP

(57) ABSTRACT

A gel composition having the formula $R^1O\text{-}[(AO)_k(EO)_m(AO)_n]\text{-}R^2$ comprises (a) 0.1 to 60 mass % of a block-type alkylene oxide derivative, (b) an oil, and (c) 0.1 to 10 mass % of water. AO represents a $C_3$-$C_4$ oxyalkylene group; EO represents an oxyethylene group; k and n represent average addition mole numbers of the oxyalkylene group and m represents average addition mole number of the oxyethylene group, $1 \leq m \leq 70$ and $1 \leq k+n \leq 70$. The oxyethylene group is 20 to 80 mass % with respect to the sum of the oxyalkylene group (AO) and the oxyethylene group. $R^1$ and $R^2$ may be identical to or different from one another and are each a $C_1$-$C_4$ hydrocarbon group or a hydrogen atom. The composition has a continuous phase comprising the oil; and the viscosity of the composition at 25° C. is 500 mPa·s or more.

6 Claims, 1 Drawing Sheet

U.S. PATENT DOCUMENTS

| | | | | |
|---|---|---|---|---|
| 3,639,574 | A * | 2/1972 | Asche | 424/62 |
| 3,691,272 | A * | 9/1972 | Henning Asche | 424/57 |
| 3,740,421 | A * | 6/1973 | Schmolka | 424/65 |
| 3,867,533 | A * | 2/1975 | Schmolka | 514/311 |
| 3,882,036 | A * | 5/1975 | Krezanoski et al. | 510/112 |
| 4,040,857 | A * | 8/1977 | Lissant | 106/243 |
| 4,163,727 | A * | 8/1979 | Inks | 507/242 |
| 4,226,889 | A * | 10/1980 | Yuhas | 424/59 |
| 4,326,977 | A * | 4/1982 | Schmolka | 510/132 |
| 4,379,095 | A * | 4/1983 | Oldack | 524/245 |
| 4,452,711 | A * | 6/1984 | Laemmle | 508/495 |
| 4,504,465 | A * | 3/1985 | Sampson et al. | 424/65 |
| 4,678,664 | A * | 7/1987 | Schmolka | 424/65 |
| 4,745,170 | A * | 5/1988 | Bushman et al. | 528/61 |
| 4,836,951 | A * | 6/1989 | Totten et al. | 510/220 |
| 4,902,575 | A * | 2/1990 | Yukimoto et al. | 428/447 |
| 4,904,466 | A * | 2/1990 | Carson et al. | 424/616 |
| 4,906,707 | A * | 3/1990 | Yukimoto et al. | 525/403 |
| 5,128,123 | A * | 7/1992 | Brewster et al. | 424/65 |
| 5,190,676 | A * | 3/1993 | Yamane et al. | 252/8.84 |
| 5,346,986 | A * | 9/1994 | Schneider et al. | 528/495 |
| 5,491,004 | A * | 2/1996 | Mudge et al. | 427/393.4 |
| 5,567,400 | A * | 10/1996 | Mudge et al. | 252/8.62 |
| 5,573,707 | A * | 11/1996 | Cole et al. | 516/129 |
| 5,593,683 | A * | 1/1997 | Viegas et al. | 424/427 |
| 5,709,852 | A * | 1/1998 | Gopalkrishnan et al. | 424/78.08 |
| 5,876,514 | A * | 3/1999 | Rolando et al. | 134/25.2 |
| 5,880,319 | A * | 3/1999 | Sloan, Jr. | 585/15 |
| 5,908,612 | A * | 6/1999 | Dailey et al. | 424/49 |
| 5,945,394 | A * | 8/1999 | Sajic et al. | 510/428 |
| 6,039,965 | A * | 3/2000 | Donlan et al. | 424/405 |
| 6,087,437 | A * | 7/2000 | Farwaha et al. | 524/555 |
| 6,130,306 | A * | 10/2000 | Kalinowski et al. | 528/34 |
| 6,176,849 | B1 * | 1/2001 | Yang et al. | 604/265 |
| 6,524,435 | B1 * | 2/2003 | Agarwal et al. | 162/1 |
| 6,548,463 | B2 * | 4/2003 | Miyahara et al. | 510/136 |
| 6,607,736 | B2 * | 8/2003 | Ohmori et al. | 424/401 |
| 6,653,436 | B2 * | 11/2003 | Back et al. | 528/335 |
| 6,818,018 | B1 * | 11/2004 | Sawhney | 623/11.11 |
| 6,866,888 | B2 * | 3/2005 | Baker et al. | 427/242 |
| 6,956,086 | B2 * | 10/2005 | Back et al. | 525/423 |
| 2001/0021691 | A1 * | 9/2001 | Miyahara et al. | 510/136 |
| 2002/0082188 | A1 * | 6/2002 | Baker et al. | 510/475 |
| 2002/0110577 | A1 * | 8/2002 | Henry et al. | 424/423 |
| 2002/0111422 | A1 * | 8/2002 | Back et al. | 524/602 |
| 2002/0119907 | A1 * | 8/2002 | Baker et al. | 510/475 |
| 2002/0121346 | A1 * | 9/2002 | Nishizaki et al. | 162/5 |
| 2003/0077245 | A1 * | 4/2003 | Henry et al. | 424/78.38 |
| 2003/0077328 | A1 * | 4/2003 | Reeve et al. | 424/486 |
| 2003/0091603 | A1 * | 5/2003 | Ohmori et al. | 424/401 |
| 2003/0092593 | A1 * | 5/2003 | Farooq et al. | 510/422 |
| 2003/0114331 | A1 * | 6/2003 | Baker et al. | 510/276 |
| 2003/0129240 | A1 * | 7/2003 | Reeve et al. | 424/486 |
| 2003/0180335 | A1 * | 9/2003 | Ohmori et al. | 424/401 |
| 2004/0063901 | A1 * | 4/2004 | Back et al. | 528/407 |
| 2004/0067322 | A1 * | 4/2004 | Baker et al. | 427/421 |
| 2004/0102350 | A1 * | 5/2004 | Baker et al. | 510/405 |
| 2005/0079188 | A1 * | 4/2005 | Ohmori et al. | 424/401 |
| 2005/0192190 | A1 * | 9/2005 | Hasenzahl et al. | 510/130 |
| 2007/0053984 | A1 * | 3/2007 | Spann-Wade et al. | 424/486 |
| 2007/0161768 | A1 * | 7/2007 | Odaka et al. | 528/25 |

FOREIGN PATENT DOCUMENTS

| | | | |
|---|---|---|---|
| JP | 1-163111 | | 6/1989 |
| JP | 7-100358 | | 4/1995 |
| JP | 8-26929 | | 1/1996 |
| JP | 08-026929 | * | 1/1996 |
| JP | 2006-28062 | * | 2/2006 |

OTHER PUBLICATIONS

Fragrance Journal, No. 33 (1978), pp. 26-31 and 126-128.

Partial English Translation of Yoshimura, "Development and Application of Liquid Fat Gelling Agents," Fragrance Journal, No. 33 (1978), four pages.

Japanese Patent Abstract for Publication No. 01-163111 published Jun. 27, 1989, one page.

Partial English Translation of JP 07-100358, ten pages.

Japanese Patent Abstract for Publication No. 08-026929 published Jan. 30, 1996, four pages.

Japanese Patent Abstract for Publication No. 2006-028062 published Feb. 2, 2006, 20 pages.

Partial English Translation of Japanese Patent Publication No. 53-27776 published Feb. 16, 1976, two pages.

International Search Report for PCT/JP2007/081420 mailed Sep. 18, 2007, two pages.

* cited by examiner

GEL COMPOSITION

RELATED APPLICATIONS

This application claims priority to Japanese Patent Application No. 2006-162028 filed on Jun. 12, 2006 and Japanese Patent Application No. 2007-11982 filed on Jan. 22, 2007, both of which are incorporated herein by reference.

FIELD OF THE INVENTION

The invention relates to gel compositions, and in particular, to an improved oil-gelling agent.

BACKGROUND OF THE INVENTION

Oil-based products, such as a cleansing oil, have a good compatibility with makeup and an excellent cleansing effect. On the other hand, oil-based products have disadvantages such as dripping when they are applied to the skin and a sticky feeling in the hands owing to oil components contained therein.

Therefore, in the fields such as cosmetics, gelation of the oil components has been used as an effective method to improve the feeling in use and stability.

More specifically, various oil-based gel compositions have been developed to solve the above-mentioned problems. For example, techniques using, as an oil-gelling agent, 12-hydroxystearic acid (refer to Patent Literature 1), N-acylamino acid amide such as N-lauroyl-L-glutamic acid dibutylamide or N-acylamino acid amine salt such as $N^\alpha,N^\omega$-dilauroyl-L-lysine stearylamine salt (refer to Patent Literature 2), polyether-modified silicones (refer to Patent Literature 3), and dextrin fatty acid ester such as dextrin palmitate (refer to Non-Patent Literature 4) have been suggested.

Patent Literature 1: Japanese Unexamined Patent Publication H1-163111
Patent Literature 2: Japanese Examined Patent Publication S53-27776
Patent Literature 3: Japanese Unexamined Patent Publication H7-100358
Non-Patent Literature 4: Atsushi YOSHIMURA, "*Development and Application of Liquid Fat Gelling Agents*", *Fragrance Journal*, No. 33 (1978), p 26-31.

Conventional gelling agents could increase the viscosity of the system. However, the system has problems such as too low viscosity, a tendency to form clumps, poor temperature stability, poor compatibility with surfactants to be blended, and difficulty retaining transparency. Furthermore, such system also has not achieved a satisfactory feeling in use.

DISCLOSURE OF THE INVENTION

Problem to be Solved by the Invention

The present invention has been conceived in view of the above-described problems, and an object thereof is to provide a gel composition having a stable gelation ability and an excellent feeling in use.

Means to Solve the Problem

The present inventors have diligently studied to achieve the above-described objects. As a result, the present inventors have found that a gel composition containing a block-type alkylene oxide derivative with a specific structure, oil components and water could achieve an excellent feeling in use, thus leading to completion of the present invention.

A gel composition of the present invention comprises:
(a) 0.1 to 60 mass % of a block-type alkylene oxide derivative,
(b) an oil, and
(c) 0.1 to 10 mass % of water;
wherein a viscosity of the composition is 500 mPa·s or more (at 25° C.); and wherein the block-type alkylene oxide derivative is represented by the following formula (I):

   (I)

wherein AO represents an oxyalkylene group having 3 to 4 carbon atoms; EO represents an oxyethylene group; l and n represent average addition mole numbers of the oxyalkylene group and m represents average addition mole number of the oxyethylene group, which are $1 \leq m \leq 70$ and $1 \leq l+n \leq 70$; the oxyethylene group is 20 to 80 mass % with respect to the sum of the oxyalkylene group having 3 to 4 carbon atoms and the oxyethylene group; and each of $R^1$ and $R^2$, which may be identical to or different from each other, is a hydrocarbon group having 1 to 4 carbon atoms or a hydrogen atom.

It is preferred that the gel composition does not comprise a conventional gelling agent.

It is also preferred that the gel composition is a transparent gel composition with an optical isotropy and 90% or more of visible light transmittance (per 1 cm optical path length) measured at 550 nm wavelength with a spectrophotometer.

Effect of the Invention

Because it contains a block-type alkylene oxide derivative, an oil component and water, the oil-based gel of the invention has a high stability, which could not be achieved with conventional gelling agents for reasons such as low viscosity or clumping. When the gel composition of the present invention is blended into products such as cosmetics, the products can be provided in usable forms without dripping during use because of excellent gelation. Moreover, such products, because they do not drip, need not be overused and may be used efficiently.

In addition, because the oil component included in the gel composition is highly dispersible, the products are more adaptable to the skin and have a good feeling in use compared with conventional products. When applying the products to the skin, it is possible to rinse them off with water easily.

Because the gel composition according to the present invention has a stable transparency, it has a good appearance and is easily blended with other compositions. Conventional products tended to get cloudy with time.

BEST MODE FOR CARRYING OUT THE INVENTION

Figure 1:
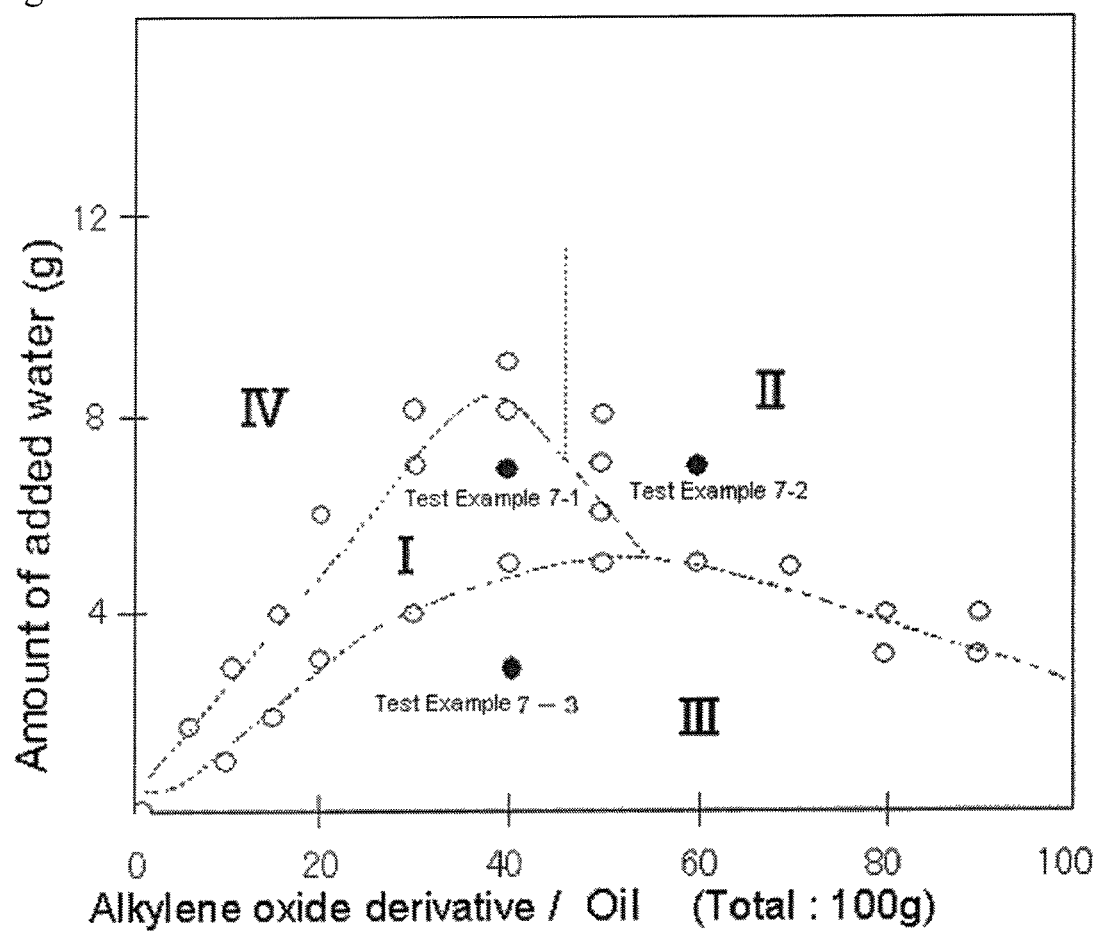
FIG. 1 is a diagram showing phases of a gel composition depending on the blending amounts of a block-type alkylene oxide derivative and water.

Hereinafter, preferred embodiments of the present invention will be described in detail.
(a) Block-Type Alkylene Oxide Derivative
A block-type alkylene oxide derivative included in the gel composition of the present invention is represented by the following formula (I):

   (I)

wherein AO represents an oxyalkylene group having 3 to 4 carbon atoms; EO represents an oxyethylene group; k and n represent average addition mole numbers of the oxyalkylene group and m represents average addition mole number of the oxyethylene group, which are $1 \leq m \leq 70$ and $1 \leq k+n \leq 70$; the oxyethylene group is 20 to 80 mass % with respect to the sum of the oxyalkylene group having 3 to 4 carbon atoms and the oxyethylene group; and each of $R^1$ and $R^2$, which may be identical to or different from each other, is a hydrocarbon group having 1 to 4 carbon atoms or a hydrogen atom.

In the above-mentioned formula (I), AO represents an oxyalkylene group having 3 to 4 carbon atoms. The specific examples of oxyalkylene group include oxypropylene group, oxybutylene group, oxyisobutylene group, oxytrimethylene group, and oxytetramethylene group, and preferably oxypropylene group or oxybutylene group. EO represents an oxyethylene group.

The value m represents the average addition mole number of the oxyethylene group, and $1 \leq m \leq 70$, preferably $5 \leq m \leq 55$. The values k and n represent the average addition mole numbers of the oxyalkylene group having 3 to 4 carbon atoms, and $1 \leq k+n \leq 70$, preferably $2 \leq k+n \leq 50$. If the number of oxyalkylene groups having 3 to 4 carbon atoms or the number of the oxyethylene group is zero, a smooth feeling in the skin is deteriorated. If it exceeds 70, a sticky feeling tends to be caused after rinsing off.

$R^1$ and $R^2$ are hydrocarbon groups having 1 to 4 carbon atoms or hydrogen atoms. Examples of hydrocarbon groups include methyl group, ethyl group, n-propyl group, isopropyl group, n-butyl group, sec-butyl group, and tert-butyl group, and preferably methyl group or ethyl group. If the hydrocarbon group has 5 or more carbon atoms, the hydrophilicity tends to decrease and the moist feeling is deteriorated.

$R^1$ and $R^2$ may be the same. Alternatively, in $R^1$ and $R^2$, a hydrocarbon group having 1 to 4 carbon atoms and a hydrogen atom may be used together, or different hydrocarbon groups having 1 to 4 carbon atoms may be used together. The same or different hydrocarbon groups having 1 to 4 carbon atoms are more preferably used. If hydrogen atoms are used in both $R^1$ and $R^2$, or a hydrocarbon and a hydrogen atom are used together in $R^1$ and $R^2$, the composition causes a more sticky feeling after being rinsed off as compared with the identical or different hydrocarbon groups having 1 to 4 carbon atoms in $R^1$ and $R^2$.

The specific examples of a block-type alkylene oxide derivative used in the present invention include POE(9)POP(2)dimethyl ether, POE(14)POP(7)dimethyl ether, POE(10)POP(10)dimethyl ether, POE(6)POP(14)dimethyl ether, POE(15)POP(5)dimethyl ether, POE(25)POP(25)dimethyl ether, POE(7)POP(12)dimethyl ether, POE(22)POP(40)dimethyl ether, POE(35)POP(40)dimethyl ether, POE(50)POP(40)dimethyl ether, POE(55)POP(30)dimethyl ether, POE(30)POP(34)dimethyl ether, POE(25)POP(30)dimethyl ether, POE(27)POP(14)dimethyl ether, POE(55)POP(28)dimethyl ether, POE(36)POP(41)dimethyl ether, POE(7)POP(12)dimethyl ether, POE(17)POP(4)dimethyl ether, POE(9)POB(2)dimethyl ether, POE(14)POB(7)dimethyl ether, POE(10)POP(10)dimethyl ether, POE(10)POP(10)dipropyl ether, POE(10)POP(10)dibutyl ether, POE(52)POB(32)dimethyl ether, POE(34)POB(14)dimethyl ether, POE(35)POB(32)dimethyl ether, POE(23)POB(32)dimethyl ether, POE(45)POB(28)dimethyl ether, POE(35)POP(30)glycol, and POE(35)POB(32)glycol.

The abbreviations POE, POP, and POB, which are used above, are for polyoxyethylene, polyoxypropylene, and polyoxybutylene, respectively. Hereinafter these abbreviations may be used.

The amount of a block-type alkylene oxide derivative blended in the gel composition of the present invention is preferably 0.1 to 60 mass %, more preferably 3 to 30 mass %. If the blending amount is less than 0.1 mass %, a satisfactory effect may not be achieved by blending. If the blending amount exceeds 60 mass %, a sticky feeling may be caused after rinsing off.

The block-type alkylene oxide derivative used in the present invention can be prepared by known methods. For example, after addition polymerization of ethylene oxide and an alkylene oxide having 3 to 4 carbon atoms to a compound with a hydroxyl group, an etherification with an alkyl halide is carried out in the presence of an alkaline catalyst to give the block-type alkylene oxide derivative.

(b) Oil

The gel composition of the present invention includes an oil component which is generally used in cosmetics, quasi-drugs and the like, such as hydrocarbon oils, higher fatty acids, higher alcohols, synthetic ester oils, and silicone oils. One or more oil components which can dissolve the alkylene oxide derivative may be used.

Examples of the hydrocarbon oils include liquid paraffin, ozokerite, squalane, pristane, paraffin, ceresin, squalene, petrolatum, and microcrystalline wax.

Examples of the higher fatty acids include lauric acid, myristic acid, palmitic acid, stearic acid, behenic acid, oleic acid, undecylenic acid, tallic acid, isostearic acid, linoleic acid, linolenic acid, eicosapentaenoic acid (EPA), and docosahexanoic acid (DHA).

Examples for the higher alcohols include linear alcohols (e.g. lauryl alcohol, cetyl alcohol, stearyl alcohol, behenyl alcohol, myristyl alcohol, oleyl alcohol, and cetostearyl alcohols); and branched-chain alcohols (e.g. monostearylglycerin ether (batyl alcohol), 2-decyltetradecinol, lanolin alcohol, cholesterol, phytosterol, hexyldodecanol, isostearyl alcohol, and octyldodecanol).

Examples of the synthetic ester oils include isopropyl myristate, cetyl octanoate, octyldodecyl myristate, isopropyl palmitate, butyl stearate, hexyl laurate, myristyl myristate, decyl oleate, hexyldecyl dimethyloctanoate, cetyl lactate, myristyl lactate, lanolin acetate, isocetyl stearate, isocetyl isostearate, cholesteryl 12-hydroxystearate, ethylene glycol di-2-ethylhexanoate, dipentaerythritol fatty acid ester, N-alkyl glycol monoisostearate, neopentyl glycol dicaprate, diisostearyl malate, glycerol di-2-heptylundecanoate, trimethylolpropane tri-2-ethylhexanoate, trimethylolpropane triisostearate, pentaerythritol tetra-2-ethylhexanoate, glycerol tri-2-ethylhexanoate, glycerol trioctanoate, glycerol triisopalmitate, trimethylolpropane triisostearate, cetyl 2-ethylhexanoate, 2-ethylhexyl palmitate, glycerol trimyristate, glycerol tri-2-heptylundecanoate, castor oil fatty acid methyl ester, oleyl oleate, acetoglyceride, 2-heptylundecyl palmitate, diisobutyl adipate, 2-octyldodecyl N-lauroyl-L-glutamate, di-2-heptylundecyl adipate, ethyl laurate, di-2-ethylhexyl sebacate, 2-hexyldecyl myristate, 2-hexyldecyl palmitate, 2-hexyldecyl adipate, diisopropyl sebacate, 2-ethylhexyl succinate, and triethyl citrate.

Examples of silicone oils include chain polysiloxanes (e.g. dimethylpolysiloxane, methylphenylpolysiloxane, and diphenylpolysiloxane); cyclic polysiloxanes (e.g. octamethylcyclotetrasiloxane, decamethylcyclopentasiloxane, and dodecamethylcyclohexasiloxane), silicone resins having a three dimensional network structure, silicone rubbers, various modified polysiloxanes (such as amino-modified polysiloxanes, polyether modified polysiloxanes, alkyl-modified polysiloxanes, fluorine-modified polysiloxanes), and acrylic silicones.

The amount of the oil component blended to the gel composition of the present invention is not restricted in particular, and in general, preferably 20 to 90 mass % with respect to the amount of the composition, and more preferably 40 to 80 mass %. If the blending amount of the oil component is less than 20 mass %, gel formation and cleansing effect may be insufficient. If it exceeds 90 mass %, a sticky feeling may be caused after use.

(c) Water

The water included in the gel composition of the present invention is not restricted in particular, and if it is to be specified, the examples of water include purified water, ion-exchanged water, and tap water.

The blending amount of water depends on the blending amount of the alkylene oxide derivative, however, preferably 0.1 to 10 mass % with respect to the amount of the composition, more preferably 0.5 to 8 mass %.

If the blending amount of water is less than 0.1 mass %, the composition may not become a gel. If it exceeds 10 mass %, water may be separated to give a clouded or hard composition or to lower the viscosity, which is practically unpreferable.

A block-type alkylene oxide derivative, which is an amphipathic substance, forms aggregates in the composition of the present invention including an oil and water. If the block-type alkylene oxide derivative and water meet specific blending amounts, the aggregates exhibit a gel-forming ability and turn the system of the composition to a gel. Thus, the gel composition of the present invention can become a gel without using other gelling agents as long as the above-mentioned essential components are included.

In the gel composition of the present invention, it is preferred that the continuous phase is an oil phase.

The word "gel" in the present invention means a state exhibiting a thixotropic property and an apparent viscosity of 500 mPa·s or more at a shear rate of 1 $s^{-1}$ at 25° C. with a cone-plate type rheometer. Hence, if the blending amounts of the block-type alkylene oxide derivative and water are within the above-mentioned ranges, and the viscosity of the composition is 500 mPa·s, the gel composition of the present invention preferably maintains a gelled state without dripping during use. If the viscosity of the composition is less than 500 mPa·s, which is not preferred, the composition does not prevent dripping.

It is preferred that the gel composition of the present invention has optical isotropy and a high transparency with visible light transmittance (per 1 cm optical path length) at 550 nm wavelength measured with a spectrophotometer of 90% or more. An optically isotropic composition has a higher thixotropy and a better feeling in use than a composition without optical isotropy. When the high-transparency gel composition of the present invention is blended to a product such as cosmetics, the visual impression of the product is good, which is preferable.

Further to the above-mentioned essential components, the components which are generally used in cosmetics or quasi-drugs, such as moisturizers, powders, surfactants, natural polymers, synthetic polymers, UV absorbers, saccharides, antioxidants, various extracts, and perfumes can be blended in the gel composition of the present invention. The gel composition can be produced in a conventional manner.

The present invention will now be described in more detail with reference to the embodiments, however, these embodiments are not intended to limit the scope of the invention.

EXAMPLES

The evaluation test method and criteria used in the embodiments are described.

<Test Method>
1. A foundation forming a strong coating prepared according to the following formulation was applied to the face over and over.

| Foundation | (mass %) |
| --- | --- |
| (1) Decamethylcyclopentasiloxane | 14.0 |
| (2) Octamethylcyclotetrasiloxane | 24.0 |
| (3) Silicone-modified pullulan | 15.0 |
| (4) Isostearic acid | 1.0 |
| (5) Titanium oxide | 5.0 |
| (6) Octyl methoxycinnamate | 5.0 |
| (7) Dextrin fatty acid-coated powder | 25.0 |
| (8) Alcohol | Balance |
| (9) Perfume | Q.S. |

2. 2 hours after applying the foundation, a sample prepared with components in the following Table 1 was applied and spread on the part where the foundation was applied to remove the makeup.
3. The sample was rinsed off with water.

<Evaluation Criteria>

Evaluation (1): Gel Forming Ability

The states of gel formation (thixotropic properties) after preparing the respective samples were observed.

The apparent viscosities at the shear rate of 1 $s^{-1}$ were measured with a cone-plate rheometer. The cone with 50 mm diameter and 2° angle was used for measurement, and the measurement temperature was 25° C. The evaluation criteria are as follows.

O: Gel having a thixotropic property is formed.
  (The viscosity is 500 mPa·s or more)
X: Gel is not formed.

Evaluation (2): Dripping Prevention Effect

Drippings of the respective samples were evaluated in Step 2 of the above-mentioned test method. The evaluation criteria are as follows.

⊚: Among 10 Panelists, 8 Panelists or more acknowledged that dripping is not sensed during use.
O: Among 10 Panelists, 6 to 7 Panelists acknowledged that dripping is not sensed during use.
Δ: Among 10 Panelists, 3 to 5 Panelists acknowledged that dripping is not sensed during use.
X: Among 10 Panelists, less than 3 Panelists acknowledged that dripping is not sensed during use.

Evaluation (3): Makeup Cleansing Effect

The makeup cleansing effects of the respective samples were evaluated in Step 2 of the above-mentioned test method. The evaluation criteria are as follows.

⊚: Among 10 Panelists, 8 Panelists or more acknowledged an excellent makeup cleansing effect.
O: Among 10 Panelists, 6 to 7 Panelists acknowledged an excellent makeup cleansing effect.
Δ: Among 10 Panelists, 3 to 5 Panelists acknowledged an excellent makeup cleansing effect.
X: Among 10 Panelists, less than 3 Panelists acknowledged an excellent makeup cleansing effect.

Evaluation (4): Smoothness

The presences of a smooth feeling in the skin after rinsing off the samples were evaluated in Step 3 of the above-mentioned test method. The evaluation criteria are as follows.

⊚: Among 10 Panelists, 8 Panelists or more acknowledged the presence of a smooth feeling in the skin after rinsing off.
O: Among 10 Panelists, 6 to 7 Panelists acknowledged the presence of a smooth feeling in the skin after rinsing off.
Δ: Among 10 Panelists, 3 to 5 Panelists acknowledged the presence of a smooth feeling in the skin after rinsing off.
X: Among 10 Panelists, less than 3 Panelists acknowledged the presence of a smooth feeling in the skin after rinsing off.

The actual use tests of the respective samples, which were prepared with the components described in the following Table 1, were conducted by 10 professional panelists with the above-mentioned test method. Gel forming abilities of the respective samples were evaluated with the criteria of the above-mentioned Evaluation Criteria (1), and the feelings in use of the compositions were tested by the panelists with the criteria of the above-mentioned Evaluation Criteria (2) to (4). The results are shown in Table 1.

TABLE 1

|  | Test Examples | | | | | |
| --- | --- | --- | --- | --- | --- | --- |
|  | 1 | 2 | 3 | 4 | 5 | 6 |
| POE(35)POB(32)dimethyl ether | 14 | — | — | — | — | 14 |
| POE(52)POB(32)dimethyl ether | — | 14 | — | — | — | — |
| Polyethylene glycol diisostearate | — | — | — | — | 14 | — |
| Polyether-modified silicone | — | — | — | 14 | — | — |
| Liquid paraffin | Balance | Balance | Balance | Balance | Balance | Balance |
| Methylphenylpolysiloxane | 2 | 2 | 2 | 2 | 2 | 2 |
| Cetyl 2-ethylhexanoate | 20 | 20 | 20 | 20 | 20 | 20 |
| Purified water | 3 | 3 | 3 | 3 | 3 | — |
| Evaluation(1) Gel Forming Ability | O | O | X | O | X | X |
| Evaluation(2) Dripping Prevention Effect | ⊚ | ⊚ | X | Δ | X | X |
| Evaluation(3) Makeup Cleansing Effect | ⊚ | ⊚ | Δ | Δ | ⊚ | ⊚ |
| Evaluation(4) Smoothness | ⊚ | ⊚ | Δ | Δ | O | ⊚ |

In Test Examples 1 and 2 in which a block-type alkylene oxide derivative and an appropriate amount of water were blended, the compositions became gels and were excellent in every evaluation.

In Test Example 3 in which a block-type alkylene oxide derivative was not blended, on the other hand, the composition did not become a gel or did not have a dripping prevention effect as well as a satisfactory makeup cleansing effect and a satisfactory smooth feeling. In Test Example 4 in which a polyether-modified silicone being an oil-gelling agent was blended instead of a block-type alkylene oxide derivative, the composition became a gel, but was inferior in feeling in use as a makeup remover to the compositions of Test Examples 1 and 2 according to the present invention. In Test Example 5 in which polyethylene glycol diisostearate being an emulsifier was used, the composition did not become a gel and did not have a dripping prevention effect.

In Test Example 6 in which water was not blended, a good makeup cleansing effect and a good feeling in use could be achieved, however, the composition did not become a gel and did not have a dripping prevention effect.

As described above, it became apparent that blending (a) a block-type alkylene oxide derivative, (b) an oil component, and (c) water could form a gel with an excellent dripping prevention effect and could give the gel composition with an excellent feeling in use.

Next, preferable blending amounts of a block-type alkylene oxide derivative with a specific structure and water to form a gel were studied.

In the composition in Table 2, the value x was changed while keeping x+y=100 g and the value z was increased from zero. The oil in Table 2 is a mixture of 73.2 parts of liquid paraffin, 2.4 parts of methylphenylpolysiloxane, and 24.4 parts of cetyl 2-ethylhexanoate. Depending on the blending amounts of the respective x, y and x components, the phase of composition varied from Phases I to IV in FIG. 1.

In the regions of Phase I and Phase II in FIG. 1, the composition was believed to become a gel. Phase III was a mono-liquid phase having optical isotropy and Phase IV consisted of two separate cloudy phases.

TABLE 2

|  | Test Example 7 |
| --- | --- |
| POE(35)POB(32)dimethyl ether | x |
| Oil | y |
| Purified water | z |

Then, samples of the respective phases in FIG. 1, Example 7-1 (from Phase I), Example 7-2 (from Phase II), and Example 7-3 (from Phase III), which were in different phases from one another, were selected and tested with the above-mentioned test method to conduct the above-mentioned evaluations (1) to (4). The results are shown in Table 3.

TABLE 3

|  | Test Example | | |
| --- | --- | --- | --- |
|  | 7-1 | 7-2 | 7-3 |
| Evaluation (1) Gel Forming Ability | O | O | X |
| Evaluation (2) Effect to prevent dripping off | ⊚ | ⊚ | X |
| Evaluation (3) Makeup Cleansing Effect | ⊚ | ⊚ | O |
| Evaluation (4) Smoothness | ⊚ | Δ | Δ |

As shown in Table 3, Test Example 7-1 from Phase I had an excellent gel forming ability, an extremely excellent dripping prevention effect, and a good feeling in use.

Test Example 7-2 from Phase II formed a gel and had an excellent dripping prevention effect. In terms of a feeling in use, however, it had slightly less smooth feeling in the skin after rinsing off than Test Example 7-1.

In Test Example 7-3 from Phase III, a gel formation could not be observed and thus a dripping prevention effect could not be achieved at all. It also had worse feeling in use than the other Test Examples.

According to the above-mentioned results, it was considered that the composition including (a) a block-type alkylene oxide derivative, (b) an oil component, and (c) water had an excellent dripping prevention effect if its physical property was correspondent to that of the composition within the regions of Phase I and Phase II in FIG. 1. That is, it was confirmed that the gel composition of the present invention includes 0.1 to 60 mass % of block-type alkylene oxide derivative and 0.1 to 10 mass % of water in the composition, wherein the continuous phase was an oil phase, and the composition was a gel having viscosity of 500 mPa·s or more.

Subsequently, to comprehend the properties of the gel compositions included in Phase I and Phase II in FIG. 1 in more details, transparencies and optical properties of the compositions in the respective phases (Test Examples 7-1 and 7-2) were investigated.

A transparency of composition was expressed in a visible light transmittance (per 1 cm optical path length) measured at 550 nm wavelength with a spectrophotometer (Hitachi U3501 spectrophotometer).

An optical property was evaluated by studying the presence of an optical isotropy in the composition in a structural observation with a polarizing microscope. The results are shown in Table 4.

TABLE 4

|  | Test Example | |
| --- | --- | --- |
|  | 7-1 | 7-2 |
| Transparency (%) | 99.6 | 99.5 |
| Isotropy | PRESENT | NONE |
| Evaluation (4) Smoothness | ☉ | Δ |

The gel composition of Test Example 7-1 within Phase I in FIG. 1 had an optical isotropy and a high transparency, and it was a transparent gel composition even in a visual observation. On the other hand, the gel composition of Test Example 7-2 within Phase II had a high transparency, but did not have an optical isotropy. The composition within Phase II, which had no optical isotropy in spite of being a gel, had slightly less smooth feeling in the skin after rinsing off.

Thus, it was confirmed that, in the gel composition of the present invention, the presence of an optical isotropy further improved a smooth feeling in the skin after rinsing off.

According to the above-mentioned results, it became apparent that, in the gel composition of the present invention, the blending amount of a block-type alkylene oxide derivative was 0.1 to 60 mass % with respect to the composition, the blending amount of water was 0.1 to 10 mass % with respect to the composition, and the viscosity was 500 mPa·s or more. Additionally, it is preferred that the gel composition has an optical isotropy and is a transparent gel composition with 90% or more of light transmittance.

Formulation examples of the gel composition of the present invention will hereinafter be described. However, the scope of the present invention is not limited by these examples. Every obtained composition became a gel effectively, could prevent dripping when taking it up on the palm, and had an excellent feeling in use.

Formulation Example 1

Cleansing Oil

|  | (mass %) |
| --- | --- |
| POE(35)POB(32)dimethyl ether | 20.0 |
| Polyethylene glycol diisostearate | 5.0 |
| Methylphenylpolysiloxane | 5.0 |
| Squalane | Balance |
| Glyceryl tri-2-ethylhexanoate | 20.0 |
| Ethanol | 0.5 |
| Perfume | Q.S. |
| Antioxidants | Q.S. |
| Purified water | 4.0 |

Formulation Example 2

Cleansing Oil

|  | (mass %) |
| --- | --- |
| POE(35)POB(32)glycol | 15.0 |
| Polyethylene glycol diisostearate | 8.0 |
| Methylphenylpolysiloxane | 3.0 |
| Liquid paraffin | Balance |
| Glyceryl tri-2-ethylhexanoate | 23.0 |
| Perfume | Q.S. |
| Antioxidants | Q.S. |
| Purified water | 3.0 |

Formulation Example 3

Hair Oil

|  | (mass %) |
| --- | --- |
| POE(34)POB(14)dimethyl ether | 30.0 |
| *Camellia* oil | Balance |
| Isononyl isononate | 10.0 |
| Cetyl 2-ethylhexanoate | 20.0 |
| Perfume | Q.S. |
| Antioxidants | Q.S. |
| Purified water | 6.0 |

Formulation Example 4

Cleansing Oil

|  | (mass %) |
| --- | --- |
| POE(52)POB(32)dimethyl ether | 15.0 |
| Polyethylene glycol dioleate | 2.0 |
| Methylphenylpolysiloxane | 2.0 |
| Cetyl 2-ethylhexanoate | 25.0 |
| Liquid paraffin | Balance |
| Perfume | Q.S. |
| Antioxidants | Q.S. |
| Purified water | 1.0 |

Formulation Example 5

Cleansing Oil

|  | (mass %) |
|---|---|
| POE(52)POB(32)dimethyl ether | 7.5 |
| POE(23)POB(32)dimethyl ether | 7.5 |
| Isononyl isononate | 20.0 |
| Liquid paraffin | Balance |
| Perfume | Q.S. |
| Antioxidants | Q.S. |
| Purified water | 4.0 |

Formulation Example 6

Cleansing Oil

|  | (mass %) |
|---|---|
| POE(45)POB(28)dimethyl ether | 15.0 |
| Polyethylene glycol diisostearate | 5.0 |
| Glyceryl tri-2-ethylhexanoate | 20.0 |
| Squalane | Balance |
| Perfume | Q.S. |
| Antioxidants | Q.S. |
| Purified water | 1.8 |

What is claimed is:

1. A gel composition comprising:
   (a) 0.1 to 60 mass % of a block-type alkylene oxide derivative,
   (b) an oil, and
   (c) 0.1 to 10 mass % of water;
   the block-type alkylene oxide derivative being represented by the following formula (I):

$$R^1O\text{-}[(AO)_k(EO)_m(AO)_n]\text{-}R^2 \quad (I)$$

wherein AO represents an oxyalkylene group having 3 to 4 carbon atoms; EO represents an oxyethylene group; k and n represent average addition mole numbers of the oxyalkylene group and m represents average addition mole number of the oxyethylene group, wherein $1 \leqq m \leqq 70$ and $1 \leqq k+n \leqq 70$; the oxyethylene group is 20 to 80 mass % with respect to the sum of the oxyalkylene group having 3 to 4 carbon atoms and the oxyethylene group; wherein each of $R^1$ and $R^2$ is a hydrocarbon group having 1 to 4 carbon atoms and may be identical or different from one another wherein the composition has a continuous phase comprising the oil; and wherein the apparent viscosity of the composition is 500 mPa·s or more (at 25° C.).

2. The gel composition according to claim 1 wherein the gel composition does not contain a gelling agent.

3. The gel composition according to claim 1, wherein the gel composition is a transparent gel composition with an optical isotropy and 90% or more of visible light transmittance (per 1 cm optical path length) measured at 550 nm wavelength with a spectrophotometer.

4. The gel composition according to claim 2, wherein the gel composition is a transparent gel composition with an optical isotropy and 90% or more of visible light transmittance (per 1 cm optical path length) measured at 550 nm wavelength with a spectrophotometer.

5. The gel composition according to claim 1, wherein $5 \leqq m \leqq 55$.

6. The gel composition according to claim 1, wherein $2 \leqq k+n \leqq 50$.

* * * * *